(12) United States Patent
Dodds

(10) Patent No.: US 7,089,932 B2
(45) Date of Patent: Aug. 15, 2006

(54) RESPIRATION MONITORING EQUIPMENT

(76) Inventor: Dennis Dodds, 10 Spring Gardens, Harwood, Bolton, BL2 3LU (GB)

( * ) Notice: Subject to any disclaimer, the term of this patent is extended or adjusted under 35 U.S.C. 154(b) by 162 days.

(21) Appl. No.: 10/482,535

(22) PCT Filed: Jun. 19, 2002

(86) PCT No.: PCT/GB02/02863
§ 371 (c)(1),
(2), (4) Date: Jun. 14, 2004

(87) PCT Pub. No.: WO03/000133
PCT Pub. Date: Jan. 3, 2003

(65) Prior Publication Data
US 2004/0233058 A1 Nov. 25, 2004

(30) Foreign Application Priority Data
Jun. 26, 2001 (GB) .................................. 0115528

(51) Int. Cl.
A61M 16/00 (2006.01)
(52) U.S. Cl. ...................... 128/202.22; 128/205.23; 128/204.18; 340/606; 340/611; 340/539.12; 600/532; 600/538
(58) Field of Classification Search ................ 340/606, 340/611, 539.12; 128/202.22, 205.23, 204.18, 128/204.23; 600/532, 538
See application file for complete search history.

(56) References Cited

U.S. PATENT DOCUMENTS 4,366,821 A * 1/1983 Wittmaier et al. .......... 600/532
5,311,875 A 5/1994 Stasz
5,765,554 A * 6/1998 Somerson et al. ...... 128/205.23
5,857,460 A * 1/1999 Popitz ................... 128/206.21
6,467,477 B1 * 10/2002 Frank et al. ........... 128/203.23

FOREIGN PATENT DOCUMENTS

WO    WO 01/43804    6/2001

* cited by examiner

Primary Examiner—Jeffery Hofsass
Assistant Examiner—Hongmin Fan
(74) Attorney, Agent, or Firm—King & Schickli, PLLC

(57) ABSTRACT

Respiration monitoring equipment comprises, in one embodiment, a medical face mask (2), adapted to be located adjacent, or to cover a patient's nostrils and/or mouth; a transducer (7) adapted to be impinged by the patient's inspired and/or expired breaths, being sensitive to the presence and/or absence of a respiratory air flow, and being capable of emitting electrical signals in accordance with the presence and/or absence of a respiratory air flow; and a monitoring unit (9) electrically connected to the transducer (7) and responsive to the presence and/or absence of signals emitted by the transducer (7), and including means of triggering at least an alarm signal in the circumstances of non-detection of respiratory air flow within one or more predetermined parameters. Another embodiment provides for "cordless" monitoring, with a transmitter unit (11) at the face mask (2) and a receiver (12) at the monitoring unit (9).

23 Claims, 3 Drawing Sheets

RESPIRATION MONITORING EQUIPMENT

FIELD OF THE INVENTION

This invention relates to respiration monitoring equipment particularly, but not exclusively for use with a subject, whether human or animal, potentially susceptible to sleep apnoea, extending also for use with patients in hospitals, ambulances and other paramedic situations. The equipment is equally suitable for veterinary use in the respiratory monitoring of animals.

BACKGROUND OF THE INVENTION

Sleep apnoea is a major hazard in people of all ages and much innovative thinking has gone to develop various techniques for detecting the occurrence of apnoea. Many complex proposals have been made in efforts to provide suitable equipment. One example is described in EP 0484174, relies on battery power, on contacts and on other components that are subject to failure. Also, the possibility of using the piezoelectric and pyroelectric properties of PVDF (poly vinylidene flouride) films for developing transducers to sense the presence or absence of breathing, is described in U.S. Pat. No. 5,311,875 which uses the PVDF film to sense the temperature differences between the inspired and expired breaths, and WO 97/05824. It is not known, however, whether any proposals have progressed beyond theory or experimentation.

Respiratory rate is one of the most important physiological parameters. It is a component of most medical and nursing records and is used in many clinical scoring systems. Extremes of respiratory rate indicate the need for urgent intervention. Even today, in the case of non-intubated patients, the measurement of respiration rate is based on human observation alone, although this is known to be highly inaccurate.

Pyroelectric sensitive transducers incorporated in a face mask can be used to provide a quantitative measure of the respiratory rate in an easy and affordable manner. Furthermore, suitable circuitry for a respiratory monitor incorporating a PVDF sensor is described in our co-pending Patent Application GB 0201095.7.

As breathing could be wholly nasal, wholly oral, or part nasal and part oral, with changes between the modes, particularly during sleep, a problem for all workers in the field is optimum creation of a transducer to ensure that the patients' breath, if breathing, will always impinge upon the transducer, so obviating any false reading.

OBJECT OF THE INVENTION

A basic object of the present invention is the provision of improved respiration monitoring equipment.

SUMMARY OF A FIRST ASPECT OF THE INVENTION

According to a first aspect of the invention, there is provided respiration monitoring equipment comprising:
  (i) a medical face mask adapted to cover a patient's nostrils and mouth;
  (ii) a transducer adapted to be impinged by the subject's inspired and/or expired breaths and sensitive to monitor the presence and/or absence of a respiratory air flow and capable of emitting electrical signals in accordance with the presence and/or absence of a respiratory air flow, and
  (iii) a monitoring unit electrically connected to the transducer and responsive to the presence and/or absence of signals emitted by the transducer, and including means of triggering at least an alarm signal in the circumstances of non-detection of respiratory air flow within one or more predetermined parameters.

PREFERRED OR OPTIONAL FEATURES OF THE FIRST ASPECT

The transducer is of a pyroelectric and piezoelectric polymer.

The polymer is PVDF.

An encoded connector is provided between the face mask and the monitor.

The encoded connector, which assists the monitoring unit to differentiate between patient types, comprises a resistor, typically a 10K resistor being employed for an adult and a 2K resistor for a child. The encoded connector can also be used to differentiate between different locations (adult-forehead and child, cheek, skin); there could be a different algorithm for babies; finally it could also differentiate between different sensor types.

The transducer is carried by the face mask.

The face mask incorporates in an adaptor collar comprising a socket, in which socket the transducer is at least in part, housed.

The adaptor collar is of a synthetic material exhibiting elastomeric characteristics.

The transducer is a push fit into the socket of an elastomeric adaptor collar.

An electrical lead extends from the transducer to the monitoring unit.

The monitoring unit comprises means to provide a prescribed time period parameter.

The monitoring unit comprises means to provide minimum and maximum air flow rate parameters.

In addition to triggering an alarm signal, the monitoring unit also comprises means to emit a "normal operation" signal, when respiratory air flow within the predetermined parameter(s) is sensed by the transducer.

SUMMARY OF A SECOND ASPECT OF THE INVENTION

According to a second aspect of the invention, of independent significance, there is provided respiration monitoring equipment comprising:
  (i) a device adapted to be located adjacent, and/or to cover, a patient's nose and/or mouth;
  (ii) a transducer carried by the device in such a location as to be impinged by the patient's inspired and/or expired breaths, being sensitive to the presence and/or absence of a respiratory air flow, and being capable of emitting signals in accordance with detection of the presence and/or absence of a respiratory air flow;
  (iii) a transmitter also carried by the device and activated by the presence or absence of signals from the transducer; and
  (iv) a remotely located receiver and monitoring unit to receive signals from the transmitter and including means of triggering at least an alarm signal in the circumstance of non-detection of respiratory air flow within one or more predetermined parameters.

ADVANTAGES OF THE SECOND ASPECT OF THE INVENTION

This aspect of the invention provides for "cordless" monitoring of a patient's respiration, and consequently, ensures not only minimal interference with a patient, but also the absence of tubing, conduits, electrical leads etc avoids the presence of components that could become deranged, detached etc during sleep, or other mal-functions, resulting in the monitoring equipment falsely switching into an alarm mode.

PREFERRED OR OPTIONAL FEATURES OF THE SECOND ASPECT

The device is an industry-standard, medical face mask.

The transducer is of a pyroelectric and piezoelectric polymer.

The polymer is PVDF.

The transducer is carried by the device.

The face mask incorporates an adaptor collar comprising a socket, in which socket the transducer is at least in part, housed.

The adaptor collar is of a synthetic plastics material exhibiting elastomeric characteristics.

The transducer is a push fit into the socket.

The transducer is housed in a length of tubing connected to, and extending from the device.

One parameter is a prescribed time period.

Other parameters are minimum and maximum air flow rates.

In addition to triggering an alarm signal, the monitoring unit also emits a "normal operation" signal, when respiratory air flow within the predetermined parameter(s) is sensed by the transducer.

BRIEF DESCRIPTION OF THE DRAWINGS

The invention will now be further described, by way of example, with reference to the accompanying drawings, in which.

DETAILED DESCRIPTION OF THE DRAWINGS

Figure 1:
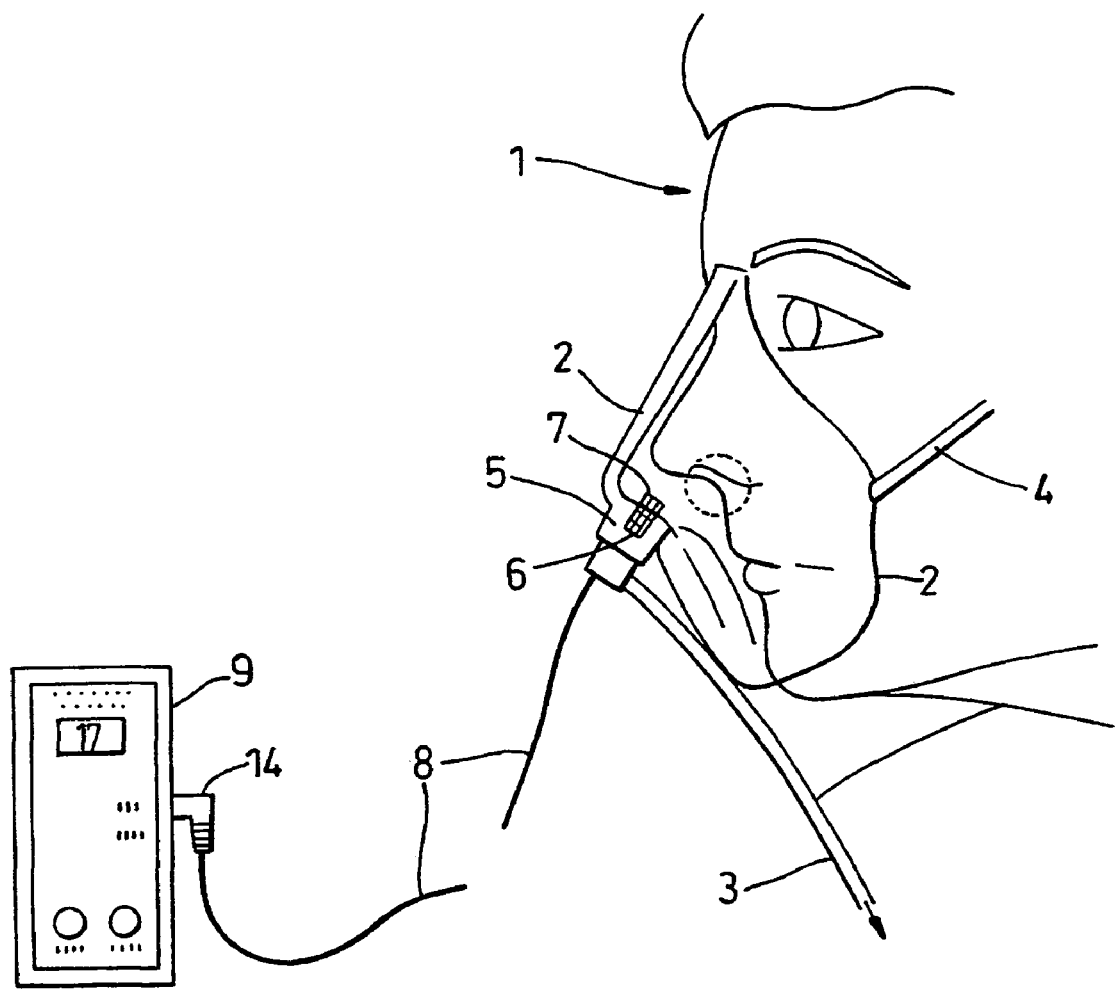
FIG. 1 is a diagrammatic side elevation of a first embodiment of equipment in accordance with the first aspect.

In all Figures, like components are accorded like reference numerals.

A head 1 of a subject is fitted with a transparent plastics, medical face mask 2 for the delivery of oxygen and/or allied therapy via a supply tube 3, the mask 2 extending over the subject's nose and mouth, and sealing against at least some portions of the subject's face under the influence of elastic loops 4 engaged over the subject's ears.

In the embodiment of FIG. 1, the face mask 2 is provided with an adaptor collar 5 of elastomeric, synthetic plastics material. The adaptor collar 5 is provided with a socket 6, in which is located a transducer in the form of a PVDF sensor 7 responsive to the air flow of the patient's breathing rhythm, the sensor 7 being in close proximity to the patient's nostrils and mouth and the presence of the mask 2 ensuring that air flow resulting from expired breaths of the subject are directed towards, and impinge upon, the transducer/sensor 7.

Any electrical output from the sensor 7 resulting from the sensing of the presence and/or absence of respiratory air flow within the predetermined parameter(s) is fed by an electrical lead 8 to a monitoring unit 9 capable of switching to an alarm mode upon the sensor 7 emitting a signal indicative of lack of air flow within a predetermined parameter, such as a prescribed time period, or possibly lack of air flow above or below a predetermined flow rate threshold. The monitor 9 can be powered either by mains electricity or by battery and may emit a local audible and/or visual alarm, when triggered and/or, if required a local alarm eg at a nursing station. An encoded connector 14 is provided between the mask 2 and the monitoring unit 9. The encoded connector 14 comprises a changeable, or switchable resistor of eg 10K for an adult patient and 2K for a child patient. Selection of the resistor can also be used to differentiate between different locations (adult-forehead and child, cheek, skin); there could be a different algorithm for babies; finally it could also differentiate between different sensor types.

Figure 2:
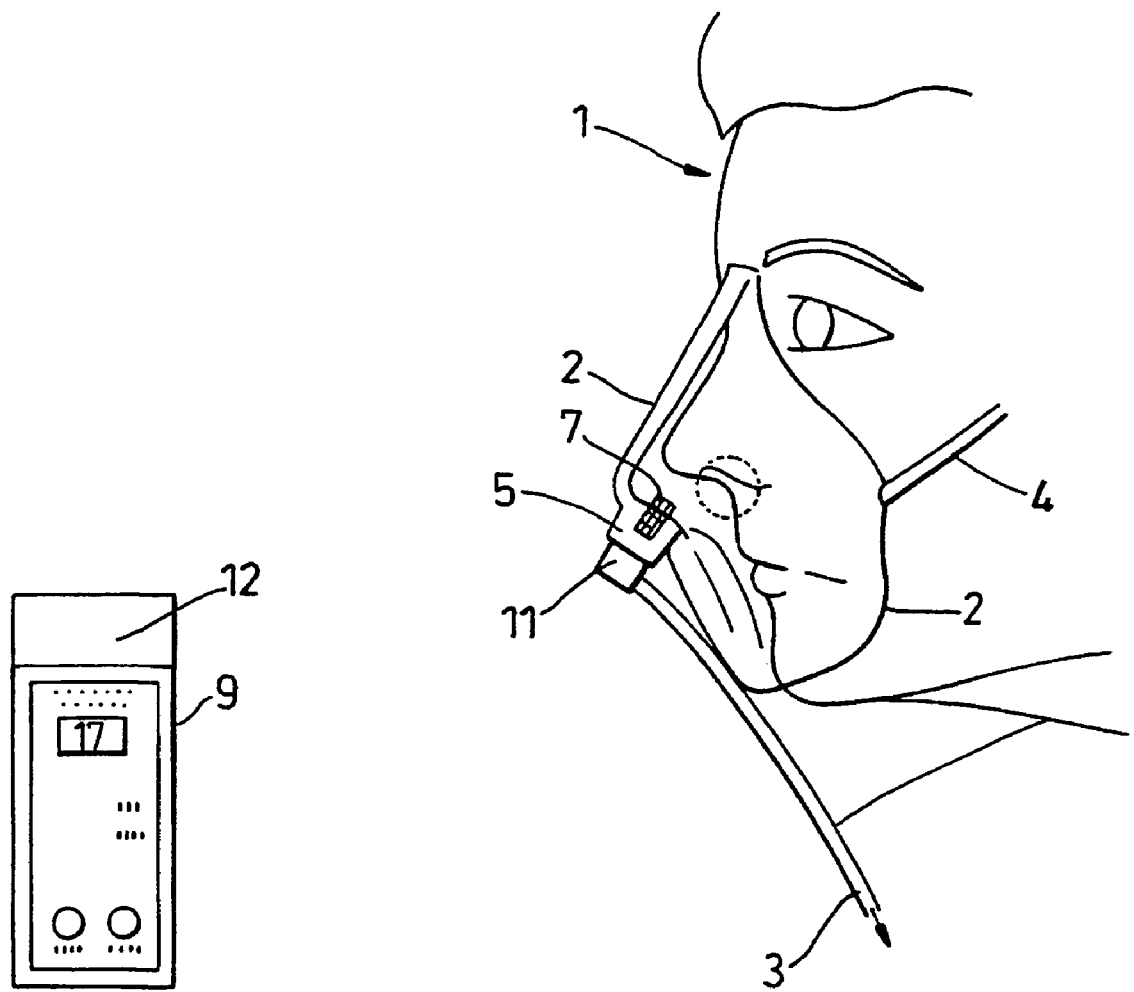
FIG. 2 is a diagrammatic side elevation of equipment in accordance with the second aspect.

The embodiment of FIG. 2 illustrates "cordless" or "wireless" respiration monitoring equipment, in which the sensor 7 is again embedded in adaptor collar 5, but the latter is provided with a transmitter unit 11 for any signals initiated by the sensor, and the monitoring unit 9 is provided with a receiver 12, the transmitter unit 11 being either battery or mains powered.

Figure 3:
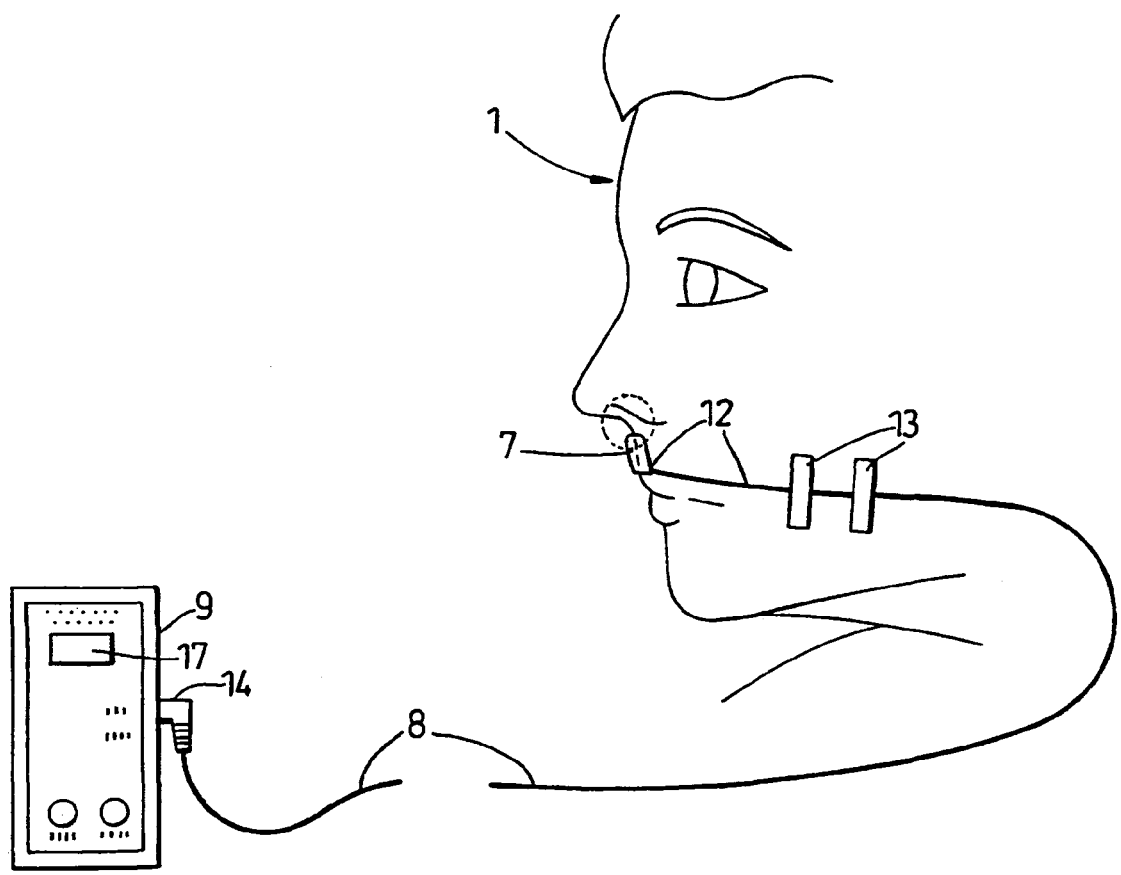
FIG. 3 is a diagrammatic side elevation of another embodiment of equipment.

Whilst the use of a device in the form of a face mask 2 channels the patient's respiratory air flow to the sensor 7, it is a fact that a generally standard face mask 2 is unsuitable for some patients, in which case the arrangement illustrated in FIG. 3 could provide a less intrusive solution, whereby the device comprises an electrical lead 8 secured eg by tapes 13 to the patient's face, extending from a sensor 7 located on the patient's upper lip to be impinged by air flow from the patient's nostrils and/or mouth, to the monitoring unit 9.

Output from the sensor 7 of FIG. 2 could alternatively follow the teachings of FIG. 2, ie by a "wireless" transmitter/receiver system.

The invention claimed is:

1. Respiration monitoring equipment comprising:
   (i) a medical face mask adapted to cover a patient's nostrils and mouth;
   (ii) a transducer adapted to be impinged by the patient's inspired and/or expired breaths, being sensitive to the presence and/or absence of a respiratory air flow, and being capable of emitting electrical signals in accordance with the presence and/or absence of a respiratory air flow,
   (iii) a monitoring unit electrically connected to the transducer and responsive to the presence or absence of signals emitted by the transducer, and including means of triggering at least an alarm signal in the circumstances of non-detection of respiratory air flow within one or more predetermined parameters; and
   (iv) an encoded connector between the face mask and the monitoring unit.

2. Equipment as claimed in claim 1, wherein the transducer is of a pyroelectric and piezoelectric polymer.

3. Equipment as claimed in claim 2, wherein the polymer is PVDF.

4. Equipment as claimed in claim 1, wherein the encoded connector comprises a resistor.

5. Equipment as claimed in claim 1, wherein the transducer is carried by the face mask.

6. Equipment as claimed in claim 1, wherein the face mask incorporates an adaptor collar comprising a socket, in which socket the transducer is at least in part, housed.

7. Equipment as claimed in claim 6, wherein the adaptor collar is of a synthetic material exhibiting elastomeric characteristics.

8. Equipment as claimed in claim 6, wherein the transducer is a push fit into the socket.

9. Equipment as claimed in claim 1, wherein an electrical lead extends from the transducer to the monitoring unit.

10. Equipment as claimed in claim 1, wherein the monitoring unit comprises means to provide a prescribed time period parameter.

11. Equipment as claimed in claim 1, wherein the monitoring unit comprises means to provide minimum and maximum air flow rate parameters.

12. Equipment as claimed in claim 1, wherein the monitoring unit also comprises means to emit a "normal operation" signal, when respiratory air flow within the predetermined parameter(s) is sensed by the transducer.

13. Respiration monitoring equipment comprising:
   (i) a medical face mask adapted to cover a patient's nostrils and mouth;
   (ii) a transducer adapted to be impinged by the patient's inspired and/or expired breaths, being sensitive to the presence and/or absence of a respiratory air flow, and being capable of emitting electrical signals in accordance with the presence and/or absence of a respiratory air flow,
   (iii) a monitoring unit electrically connected to the transducer and responsive to the presence or absence of signals emitted by the transducer, and including means of triggering at least an alarm signal in the circumstances of non-detection of respiratory air flow within one or more predetermined parameters; and
   (iv) an encoded connector comprising a resistor between the face mask and the monitoring unit.

14. Equipment as claimed in claim 13, wherein the transducer is of a pyroelectric and piezoelectric polymer.

15. Equipment as claimed in claim 14, wherein the polymer is PVDF.

16. Equipment as claimed in claim 13, wherein the transducer is carried by the face mask.

17. Equipment as claimed in claim 13, wherein the face mask incorporates an adaptor collar comprising a socket, in which socket the transducer is at least in part, housed.

18. Equipment as claimed in claim 17, wherein the adaptor collar is of a synthetic material exhibiting elastomeric characteristics.

19. Equipment as claimed in claim 17, wherein the transducer is a push fit into the socket.

20. Equipment as claimed in claim 13, wherein an electrical lead extends from the transducer to the monitoring unit.

21. Equipment as claimed in claim 13, wherein the monitoring unit comprises means to provide a prescribed time period parameter.

22. Equipment as claimed in claim 13, wherein the monitoring unit comprises means to provide minimum and maximum air flow rate parameters.

23. Equipment as claimed in claim 13, wherein the monitoring unit also comprises means to emit a "normal operation" signal, when respiratory air flow within the predetermined parameter(s) is sensed by the transducer.

* * * * *